United States Patent [19]
Ginn et al.

[11] Patent Number: 5,891,140
[45] Date of Patent: Apr. 6, 1999

[54] ELECTROSURGICAL DEVICE FOR HARVESTING A VESSEL ESPECIALLY THE INTERNAL MAMMARY ARTERY FOR CORONARY ARTERY BYPASS GRAFTING

[75] Inventors: Richard S. Ginn, San Jose; Charles S. Taylor, San Francisco, both of Calif.; Michael D. Hooven, Cincinnati, Ohio

[73] Assignee: Cardiothoracic Systems, Inc., Cupertino, Calif.

[21] Appl. No.: 773,298

[22] Filed: Dec. 23, 1996

[51] Int. Cl.⁶ .................................................... A61B 17/36
[52] U.S. Cl. ................................................. 606/48; 606/45
[58] Field of Search ............................... 606/45–52, 170, 606/205–207

[56] References Cited

U.S. PATENT DOCUMENTS

| | | |
|---|---|---|
| 4,101,063 | 7/1978 | Kapitanov et al. . |
| 4,607,622 | 8/1986 | Fritch et al. ............................. 600/104 |
| 4,638,802 | 1/1987 | Okada . |
| 5,013,312 | 5/1991 | Parins et al. . |
| 5,141,519 | 8/1992 | Smith et al. . |
| 5,152,778 | 10/1992 | Bales, Jr. et al. . |
| 5,171,256 | 12/1992 | Smith et al. . |
| 5,174,300 | 12/1992 | Bales et al. . |
| 5,192,298 | 3/1993 | Smith et al. . |
| 5,219,357 | 6/1993 | Honkanen et al. . |
| 5,241,968 | 9/1993 | Slater . |
| 5,250,047 | 10/1993 | Rydell . |
| 5,254,115 | 10/1993 | Bhatta et al. . |
| 5,290,287 | 3/1994 | Boebel et al. . |
| 5,290,309 | 3/1994 | Kothe . |
| 5,334,198 | 8/1994 | Hart et al. ................................ 606/52 |
| 5,342,359 | 8/1994 | Rydell . |
| 5,342,381 | 8/1994 | Tidemand . |
| 5,350,391 | 9/1994 | Iacovelli ................................. 606/170 |
| 5,352,222 | 10/1994 | Rydell ..................................... 606/52 |
| 5,352,223 | 10/1994 | McBrayer et al. . |
| 5,366,467 | 11/1994 | Lynch et al. . |
| 5,383,876 | 1/1995 | Nardella . |
| 5,391,166 | 2/1995 | Eggers . |
| 5,395,386 | 3/1995 | Slater . |
| 5,437,664 | 8/1995 | Cohen et al. . |
| 5,445,638 | 8/1995 | Rydell et al. . |
| 5,456,684 | 10/1995 | Schmidt et al. . |
| 5,458,598 | 10/1995 | Feinberg et al. ......................... 606/52 |
| 5,480,409 | 1/1996 | Riza . |
| 5,484,435 | 1/1996 | Fleenor et al. . |
| 5,484,436 | 1/1996 | Eggers et al. ............................ 606/48 |
| 5,496,312 | 3/1996 | Klicek .................................... 606/51 |
| 5,501,698 | 3/1996 | Roth et al. ............................. 606/205 |
| 5,514,134 | 5/1996 | Rydell et al. . |
| 5,540,685 | 7/1996 | Parins et al. . |
| 5,569,243 | 10/1996 | Kortenbach et al. ..................... 606/46 |
| 5,573,534 | 11/1996 | Stone . |
| 5,573,535 | 11/1996 | Viklund . |
| 5,637,111 | 6/1997 | Sutcu et al. ............................. 606/51 |
| 5,658,281 | 8/1997 | Heard ..................................... 606/48 |

OTHER PUBLICATIONS

"Tissue Actions of Bipolar Scissors Compared with Monopolar Devices," MSBaggish; RDTucker Techniques and Instrumentation, vol. 63, No. 2, Feb. 1995, pp. 422–426.
Entire Family of Everest Bipolar Instruments Product Brochure, Aug. 1995.

*Primary Examiner*—Michael Peffley
*Attorney, Agent, or Firm*—Lyon & Lyon LLP

[57] ABSTRACT

Devices and methods for minimally invasive harvesting of a vessel, especially the internal mammary artery for coronary artery bypass grafting, are disclosed. Generally, an electrosurgical instrument is provided which has a scissors mechanism or other end effector for dissecting tissue. The instrument also has monopolar or bipolar capabilities. Bipolar blade configurations provide current flow between blades or within each blade of the scissors mechanism or both. The instrument includes at least one ergonomically positioned actuator for actuating movement of the blades or end effectors for cutting tissue, for actuating current flow for cauterizing tissue, or for simultaneously or sequentially actuating movement and current flow. In one embodiment, the actuator is operable by a fingertip. The instrument also has a shaft which extends between the scissor mechanism and a handle portion which may be selectively rotatable or malleable to optimize orientation of the scissor mechanism.

9 Claims, 5 Drawing Sheets

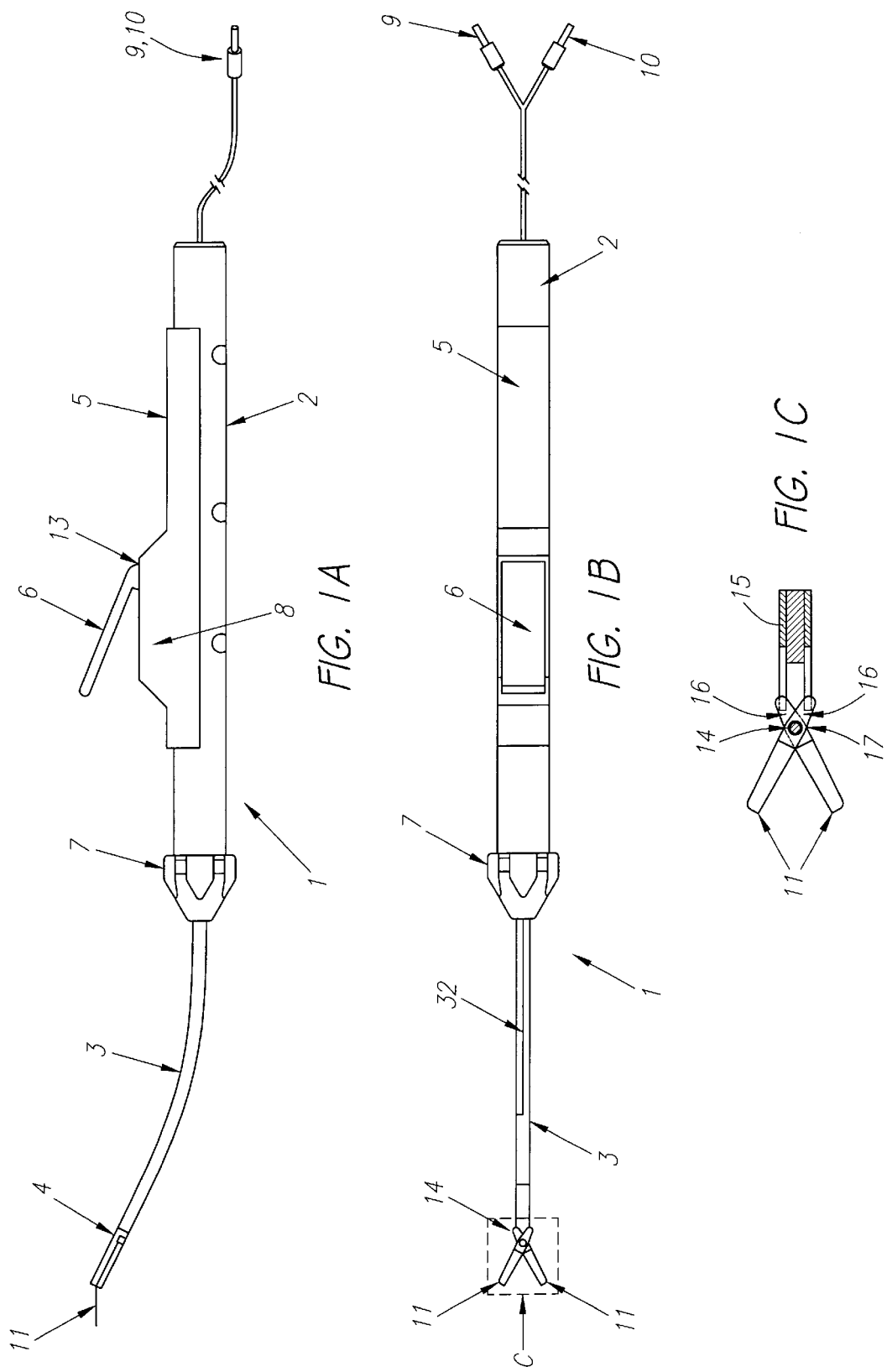

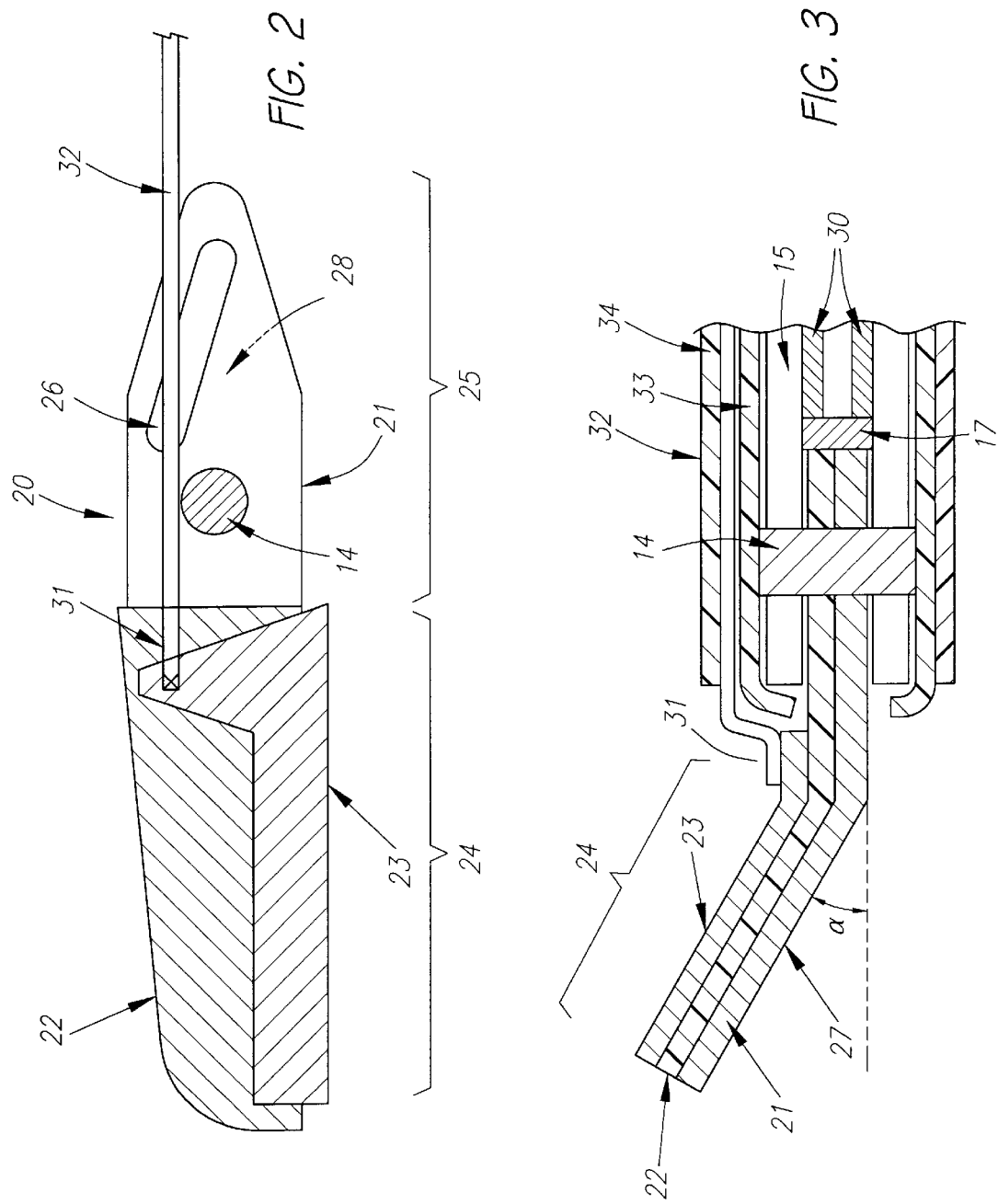

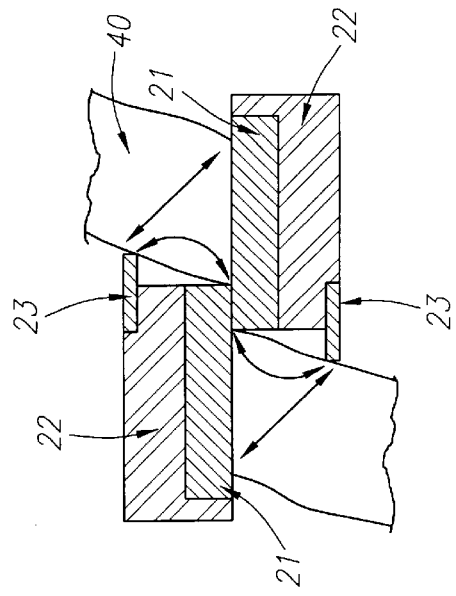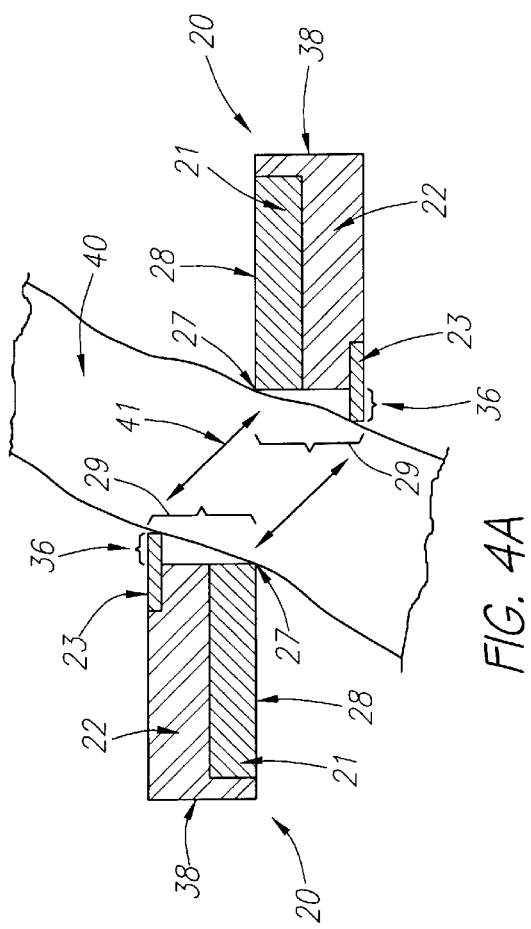

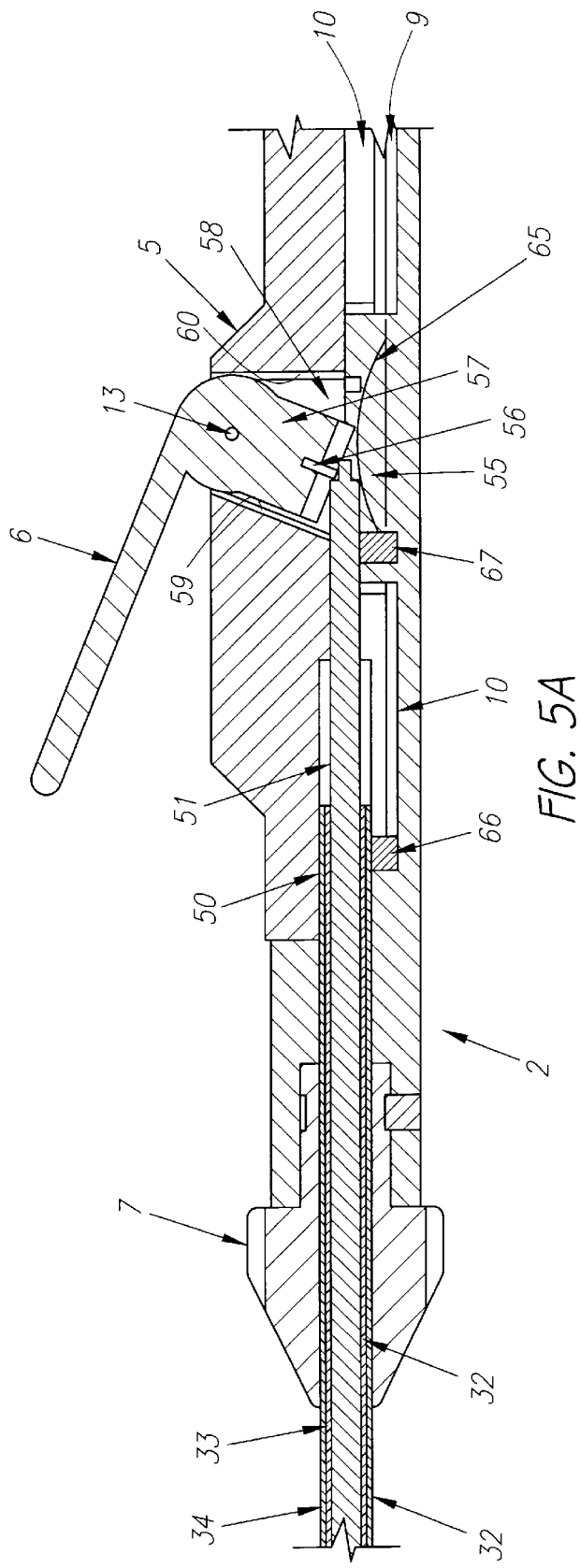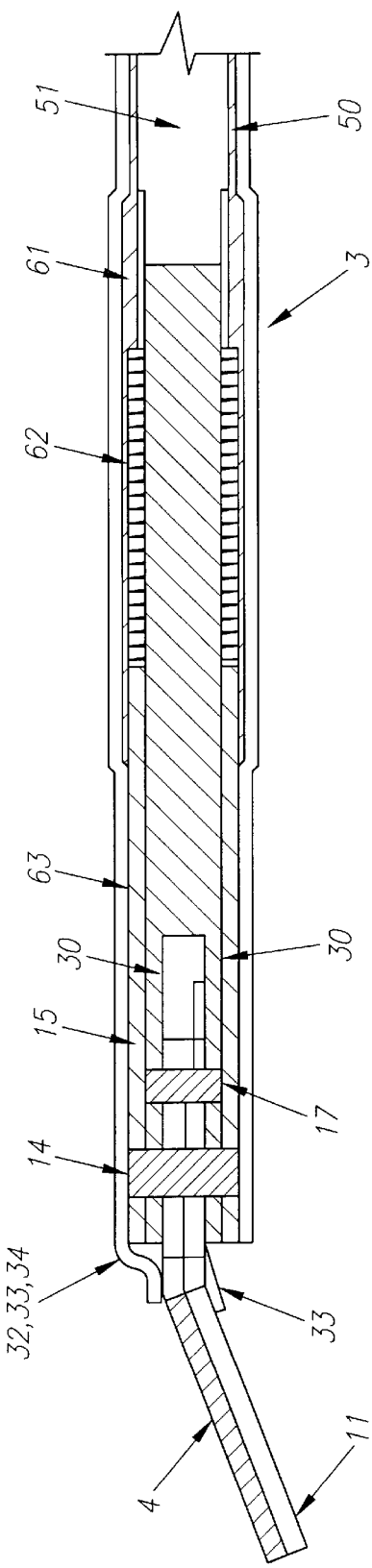
FIG. 5A
FIG. 5B

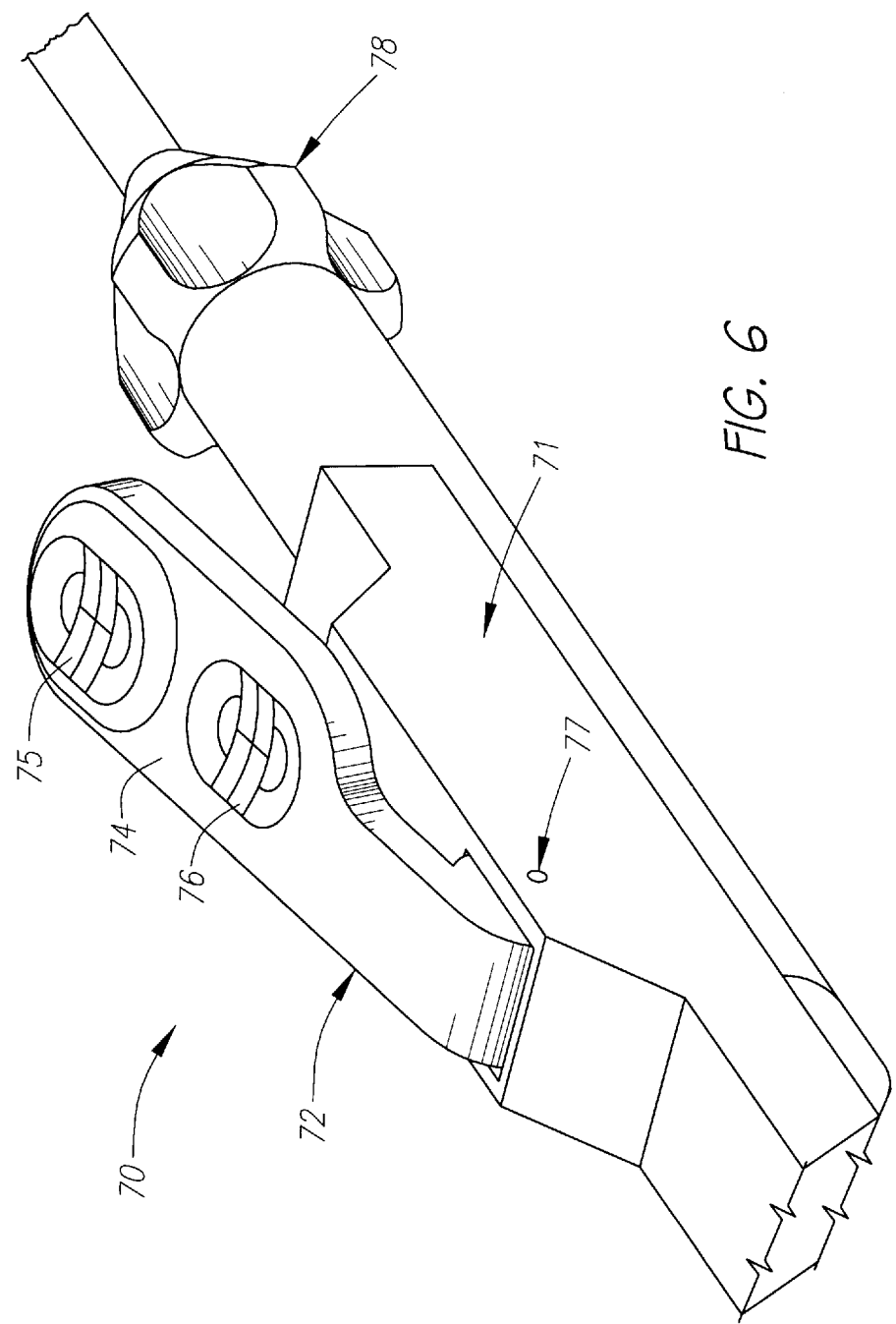

ELECTROSURGICAL DEVICE FOR HARVESTING A VESSEL ESPECIALLY THE INTERNAL MAMMARY ARTERY FOR CORONARY ARTERY BYPASS GRAFTING

FIELD OF THE INVENTION

This invention relates generally to an electrosurgical device, and more particularly to an electrosurgical instrument for harvesting the internal mammary artery or the like for use in coronary artery bypass grafting.

BACKGROUND OF THE INVENTION

A particularly prevalent form of cardiovascular disease is atherosclerosis which creates a restriction or blockage of the blood flow in the cardiovascular system leading to the heart. Vascular complications produced by atherosclerosis, such as stenosis, aneurysm, rupture or occlusion, in which the atherosclerosis is advanced and the health of a patient is jeopardized, call for surgical intervention. In many cases, a blockage or restriction of the blood flow leading to the heart can be treated by a coronary artery bypass graft (CABG) procedure.

In a CABG procedure, the obstruction is bypassed by a vascular conduit established between an arterial blood source and the coronary artery to be bypassed at a location beyond the obstruction. The vascular conduit is typically a non-critical artery or vein harvested from elsewhere in the body. Often, the saphenous vein, harvested from the patient's leg, is used as the vascular conduit wherein one end of the vein is anastomosed to the aorta and the other end is anastomosed to the diseased coronary artery at a location distal to the obstruction. This procedure is known as a "free bypass graft." Alternatively, an "in situ bypass graft" procedure may be employed, wherein an artery proximate the heart is used as the bypass conduit. In an in situ bypass graft procedure, the surgeon dissects a sufficient length of the artery from its connective tissue, then transects the artery, and connects the transected end to the diseased coronary artery distal to the obstruction while leaving the other end attached to the arterial supply, thus restoring blood flow to the heart. Recent studies have shown that it is preferable to use a pedicled or transected arterial conduit, rather than a harvested vein, as they tend to have a better patency rate than free bypass grafts. Two other obvious advantages of in situ bypass grafts over free bypass grafts is that they require only one anastomotic connection rather than two, and they are accessible through the thoracic cavity, obviating the need for incisions elsewhere in the body.

The internal mammary arteries (IMAs), left (LIMA) and right (RIMA), are particularly desirable for use as in situ bypass grafts as they are conveniently located, have diameters and blood flow volumes that are comparable to those of coronary arteries, and typically have superior patency rates. Extending from the subclavian arteries near the neck to the diaphragm and running along the backside of the ribs adjacent the sternum, the IMAs deliver blood to the musculature of the chest wall. The LIMA is suitable as an arterial source for target locations on the left anterior descending coronary artery (LAD), the diagonal coronary artery (Dx), the circumflex artery (Cx), the obtuse marginal artery, and the ramus intermedius coronary artery. The RIMA is available for connection to all of the same target locations, as well as the right coronary artery and the posterior descending artery.

Use of either IMA as a bypass graft first involves harvesting the IMA free from the chest wall. In conventional CABG approaches, access to the IMA is obtained through a sternotomy or major thoracotomy. Typically an electrosurgical tool (often called a "Bovie") is used to free a length of the IMA by incising the endothoracic fascia to free the IMA. The use of such electrosurgical devices is well known in the art and can be crucial in controlling bleeding during harvesting of the IMA. Such devices are typically in the form of scalpels, forceps, and scissors, and employ at least one conductive electrode connected thereto. Radio frequency (RF) energy is conducted through this electrode to either a remote return electrode in the form of a body plate (monopolar technology) or to a second, closely-spaced conductive electrode (bipolar technology). Current passing through the gap between the two electrodes coagulates blood while separating tissue placed between the two electrodes. Because radio frequency (RF) energy is passed through the patient's body in monopolar electrosurgery, there is a greater potential for unintended injury to body tissues as the electrical current passes through them to the return electrode. Bipolar electrosurgical devices provide an improved margin of patient safety as both the active and return electrodes are located on the surgical instrument itself, not requiring the RF energy to travel through unrelated tissue. An example of a bipolar scalpel is disclosed in U.S. Pat. No. 5,013,312.

Utilizing an electrosurgical device such as the bipolar instruments described above, a surgeon cuts away or dissects a section of the IMA, usually about 10 to 20 cm in length, from the surrounding fascia with the target vessel still intact. As the IMA is freed from the fascia, the side branches of the IMA are then cut or cauterized. A section of the IMA is chosen which, when cut distally, will reach the desired anastomosis site on the diseased coronary artery to be bypassed, typically the LAD. A removable clamp is then applied to the IMA near the distal end of the mobilized section but proximal to the point at which the vessel is to be transected. The clamp temporarily occludes the IMA and is later removed to reestablish blood flow once the anastomotic connection has been made. One or more surgical clips are then applied to the IMA distal to the point at which it is to be transected. After the clips are applied, scissors or other cutting devices are then used to transect the IMA near the distal end of the mobilized section between the removable clamp and the surgical clips, creating a free end. The "pedicled graft" is then attached to the targeted diseased coronary artery while the proximal portion of the IMA remains attached to the subclavian artery. Once the anastomosis is complete, blood flow is initiated through the graft vessel by removing the clamp from the IMA.

With conventional CABG, harvesting of the IMAs is accomplished with relative ease due to the working space made available by sternotomy or major thoracotomy. Recently, progress has been made in advancing minimally invasive surgical techniques, particularly in cardiothoracic surgery, which eliminate the need for a sternotomy or major thoracotomy. Access to the heart with these minimally invasive techniques is obtained through one very small surgical incision or through several percutaneous cannulas known as trocar sleeves positioned intercostally in the thoracic cavity of the patient. Visualization of the operative area may be facilitated by thoracoscopes which typically consist of a video camera configured for introduction through a small incision or trocar sleeve to allow observation of the target area on a video monitor.

With the advent of these minimally invasive techniques, harvesting the IMA has become more complex and difficult due to restricted work space and access, and to reduced visualization of the IMA. This is a concern as a high degree of precision is required when harvesting a bypass vessel to avoid injury (such as over cutting or cauterizing) to the vessel which may in turn lead to increased rates of occlusion in the vessel in the months and years after the procedure.

Although many low-profile surgical instruments, and particularly electrosurgical devices, such as bipolar forceps and scissors for cauterizing and/or cutting tissue and vessels, have been developed to aid in minimally invasive surgery on organs and ducts of the abdominal and pelvic cavities, such has not been the case for harvesting the IMA and other similarly situated arteries in minimally invasive CABG procedures. Surgical instruments designed for laparoscopic and other minimally invasive applications are not generally suitable for performing minimally invasive CABG. Most laparoscopic procedures, for example, target body structures which are quite large in comparison to coronary vessels, and do not require the high degree of precision required in a CABG procedure. Accordingly, laparoscopic instruments generally have lengths which are too short, are very straight, and provide only limited angular orientation, making them unsuitable for harvesting of the IMA through a minimal thoracotomy or an intercostal puncture site. Furthermore, such laparoscopic instruments have relatively large end-effectors (e.g., blades) with relatively large ranges of movement, making such instruments ill-suited for use in IMA harvesting in minimally invasive CABG procedures. In addition, such instruments commonly have finger loops or pistol-type actuators gripped in the user's palm or between the user's thumb and forefinger, such as the bipolar scissors and forceps disclosed in U.S. Pat. Nos. 5,540,685 and 5,445,638, respectively, limiting the sensitivity and precision with which such instruments can be manipulated and actuated. Such finger loops or pistol-type grips also are limited to a single orientation in the user's hand and cannot be repositioned in the hand to allow better access to a body structure or to change the orientation of the end-effector.

It is therefore an object of the present invention to provide an improved electrosurgical device for the hemostatic harvesting of arteries to be used for minimally invasive CABG procedures.

Another object of the present invention is to provide an electrosurgical device having a suitable profile, length, and angular orientation for introduction through a small incision or surgical puncture and for reaching the LIMA, RIMA or similarly situated artery.

Another object of the present invention is to provide an electrosurgical instrument having end-effectors which have very small dimensions and are capable of very subtle ranges of motion.

Still another object of the present invention is to provide an electrosurgical instrument that provides ergonomic, comfortable, and sensitive actuation by one finger.

Another object of the present invention is to provide an electrosurgical instrument which allows for multiple orientations in a user's hand.

It is also an object of the present invention to provide a method of harvesting a vessel which provides for cutting and/or cauterizing of tissue by means of a finger activated actuator.

SUMMARY OF THE INVENTION

In accordance with the present invention, various embodiments of an electrosurgical tool are provided for the minimally invasive harvesting of a vessel, particularly a vessel to be used for a CABG procedure such as an IMA. In general, the electrosurgical tool includes an elongated shaft having proximal and distal ends, a handle portion connected at the proximal end, and an end effector joined at the distal end. The end effectors may be any pair of coacting members, such as blades or forceps, and may provide monopolar or bipolar capabilities for creating hemostasis of tissue coming into contact with the end effectors. The end effector has active and inactive positions with each blade having at least one electrode adapted for connection to a voltage source. The voltage source has a pair of terminals of opposite polarity whereby current flow between the electrodes promotes hemostasis in tissue contacting the scissor blades. At least one actuator is operably connected to the end effector and is positioned on the handle to be operable by a user's fingertip on the hand with which the tool is held. The actuator effects movement of the end effector between the active and inactive positions and actuates current flow through the electrodes. Movement of the end effector may occur either simultaneously or sequentially with actuation of the current flow.

A preferred embodiment includes a bipolar electrosurgical tool comprising an elongated shaft having proximal and distal ends, a pair of blades joined for relative movement in a scissor-like action between open and closed positions at the distal end of the shaft. Each the blade includes first and second spaced apart electrodes extending along the blade which are adapted for connection to a voltage source having a pair of terminals of opposite polarity whereby current flow between the first and second electrodes of each blade promotes hemostasis in tissue contacting the blades. The tool further includes a handle operatively connected to the proximal end of the shaft, and at least one actuator operably connected to the blades and positioned on the handle so as to be operable by a user's fingertip on the hand with which the tool is held. The actuator is used for effecting the relative movement of the blades and for actuating current flow through the electrodes of each blade.

The bipolar electrosurgical tool may also include the capability to rotate the elongated shaft with respect to the handle in order to more effectively orient the blades for dissection of the vessel. For example, one embodiment provides a knob positioned coaxially between the proximal end of the shaft and the handle which, when turned, rotates the shaft. The shaft may be straight or curved, and may also be malleable for optimizing positioning of the blades.

The end effectors, such as blades, of the bipolar embodiments may have various electrode configurations. In a preferred embodiment, however, electrically insulative material is disposed between the electrodes. Also, the first electrodes of each blade are adapted to be connected to one terminal of the voltage source such that the first electrodes are of like polarity and the second electrodes of each blade are adapted to be connected to the same terminal of the voltage source such that the second electrodes are of like polarity. Both of the first electrodes are adapted for connection to the same terminal of the voltage source such that the first electrodes are of like polarity, and similarly, the second electrodes are of like polarity. The electrode surfaces may be disposed such that current flows substantially between the first and second electrode surfaces of each blade or substantially between the first electrode of one blade and the second electrode of the other blade.

The bipolar electrosurgical tool of the present invention may comprise one or more low-profile, ergonomically positioned actuators for actuating the movement of the blades, or actuating bipolar activity, or both. In one embodiment, one actuator is provided which comprises two depressible positions, a first depressible position for causing the first electrodes to be connected to one terminal and the second electrodes to be connected to the other terminal of the voltage source and a second depressible position for causing the blades to close. Preferably, the actuator is operable by a finger, such as the index finger, and the force necessary to achieve the first depressible position is less than the force necessary to achieve the second depressible position.

Additionally, the bipolar electrosurgical tool may further include a second actuator for causing the blades to close, whereby both of the actuators are operable by the same finger, one actuator is operable by a finger and the other by a thumb, or one is operable by a finger or a thumb and the other is operable by the user's foot.

In some embodiments, the blades may extend at an acute angle from the axis of rotation of the elongated shaft, and preferably at an angle between about 0 and 35 degrees. Alternatively, the blades may be curved.

The present invention also provides a method for harvesting a vessel, especially arteries such as the left and right internal mammary arteries. In one embodiment, the method includes providing an instrument comprising a pair of distal coacting members, which are joined for relative movement between open and closed positions and include at least one depressible actuator operably connected to the distal coacting members, contacting tissue adjacent the vessel with the distal coacting members, depressing the actuator with a finger, providing current flow between the members, and actuating the relative movement. The method may further include depressing the actuator with a finger after providing current flow between the members for sequential actuation of current flow and relative movement between the coacting members.

These and other embodiments and modifications of the present invention are set forth in the following detailed description and drawings.

BRIEF DESCRIPTION OF THE DRAWINGS

FIGS. 1A and 1B are side and top views, respectively, of an embodiment of an electrosurgical instrument, in accordance with the present invention.

FIG. 1C is an enlarged sectional view of the scissor mechanism of FIG. 1B.

FIG. 2 is enlarged, schematic top view of one blade of the scissor mechanism embodiment of FIG. 1C.

FIG. 3 is an enlarged, schematic cross-sectional side view of one of the blades and distal portion of the scissor mechanism of the embodiment of FIGS. 1A–C.

FIGS. 4A–C are vertical cross-sectional view of an embodiment of the scissor blades of FIG. 2. FIG. 4A illustrates the bipolar operation of the blades as they move from an open position in contact with the tissue to be cut, to an intermediate position in FIG. 4B, just after the tissue is cut, and to a fully closed position in FIG. 4C.

FIG. 5A is a horizontal cross-sectional side view of the handle portion of the embodiment of FIGS. 1A–C.

FIG. 5B is a horizontal cross-sectional side view of the shaft and blade portions of the embodiment of FIGS. 1A–C.

FIG. 6 is an enlarged perspective view of the handle portion of FIG. 1A including an exemplary embodiment of the scissor and bipolar actuation mechanism according to the present invention.

DETAILED DESCRIPTION OF THE INVENTION

Referring to FIGS. 1A and 1B, there is indicated generally by the numeral 1, an electrosurgical instrument, constructed in accordance with the present invention, for harvesting of vessels for coronary artery bypass grafting, and particularly adapted for harvesting the IMAs. Electrosurgical instrument 1 generally includes a handle means 2, an end effector 4, and an elongated shaft 3 extending therebetween. The overall length of instrument 1 from the distal end, meaning remote from handle 2 and at the site where the harvesting procedure is performed, to the proximal end of handle 2 is between about 30 and 35 cm. The length of handle 2 and shaft 3 are each between about 15 and 17 cm, and the length of scissor mechanism 4 is between about 1 and 2 cm, however, each of these lengths may be longer or shorter depending on the application.

At the proximal end of instrument 1 is handle portion 2 which is adapted to be held in the hand for manipulation of instrument 1 when introduced through a minimally invasive incision. Handle 2 includes a cover 5 extending longitudinally over a substantial portion of handle 2 and having an elevated portion 8. An actuator in the form of a lever 6 is pivotally mounted to cover 5 on elevated portion 8 by means of a fulcrum mechanism 13 or other pivoting means for providing remote actuation of scissors mechanism 4, described in detail below. Other means for actuating the scissors mechanism 4, such as a trigger or slide switch, are also contemplated for use with the instrument of the present invention.

At the distal end of instrument 1 is the end effector in the form of scissors mechanism 4 having a pair of coacting blades 11, which provide the ability to separate a vessel from surrounding tissue and to selectively make incisions proximate to the distal end of instrument 1. In FIG. 1C, which is an enlargement of the portion of instrument 1 within box C of FIG. 1B, blades 11 are shown to be pivotally fixed to shaft 3 and each other by means of and pivots about a pivot pin 14. Each blade 11 is slotted, having a slot 16 within which resides a sliding pin 17. Sliding pin 17 slides within slots 16 to provide relative movement of blades 11 between open and closed positions or active and inactive positions. Sliding pin 17 is connected to the distal end of an actuator rod 15 or rigid wire which extends through tubular shaft 3, as depicted in FIG. 1A. Axial movement of actuator rod 15, which is controlled by lever 6, closes and opens blades 11. This function will be described in more detail below. Although a particular type of scissor mechanism is illustrated in the drawings, the present invention is not limited to this type of mechanism, and any other scissors having a pair of movable blades or other type of tool having coacting members (such as forceps) may be employed with the present invention.

In FIG. 1A, extending between blades 11 and the proximal end of handle 2, is elongated shaft 3. Shaft 3 is shown having a curved configuration and oriented such that end effector 4 is pointing upward relative to handle 2; however, shaft 3 may also have a straight configuration. A curved shaft may be advantageous when harvesting an IMA through a minimal thoracotomy or an intercostally positioned trocar sleeve as the IMA, in its natural site, may lie in the same plane with such surgical openings. Accordingly, shaft 3 and any components housed within or externally engaged with shaft 3 may be made of a malleable material, such as aluminum, so as to be selectively bendable to facilitate delivery of instrument 1 through a minimally invasive opening and to provide optimum orientation of scissor mechanism 4 for dissecting a vessel.

Between the proximal end of shaft 3 and the distal end of handle 2 is a rotation mechanism 7, illustrated in the form of a rotatable knob, for rotating shaft 3 with respect to handle 2. Rotation mechanism 7 may be manually manipulated or may be electrically activated, and may be in the form of a switch, dial, button or other means. By either means, the orientation of curved shaft 3 and scissors mechanism 4 can be selectively adjusted to provide optimal access to the vessel during the harvesting procedure. Thus, any tissue structure extending from or surrounding a vessel may be positioned between blades 11 by rotation of handle 2 or by independent rotation of rotation mechanism 7.

Extending from the proximal end of handle 2 are a pair of leads 9 and 10, each comprising a coaxially insulated contact wire whose proximal ends are adapted to be connected to a voltage source, such as to the bipolar terminals (of opposite polarity) of a commercially available RF energy source (not shown). Handle 2 has an inner lumen (see FIG. 5A) through which contact wires extend and are operably coupled to electrodes on blades 11, in a manner as will be described below, whereby current flow between the electrodes causes hemostasis in tissue contacting the surfaces of blades 11. As used herein, hemostasis generally means the arresting of bleeding including coagulation and cauterization.

Referring now to FIGS. 2 and 3, there are shown enlarged, vertical and horizontal cross-sectional views of the blade assembly of the exemplary scissor mechanism of FIG. 1C. Each blade 20 includes an inner conductive blade element 21 which defines the distal end of a first electrode, an intermediate layer of insulative material 22, and an outer conductive blade element 23 which defines the distal end of a second electrode. The inner blade element 21 includes a distal segment 24 and a proximal segment 25. Distal segment 24 may be curved or straight, and is preferably angled from the axis of rotation of elongated tubular shaft 30. Preferably, the angle α is between about 0° and 35°, but may be more than 35°. Proximal segment 25 is received within the distal end of shaft 30 and is mounted to a pivot pin (not shown) which fits within slot 26.

The inner blade element or first electrode 21 of each blade 20 is preferably metal, such as stainless steel, or other suitable material that is of high strength and will hold a sharp cutting edge for repeated use. Insulative material 22 completely separates inner blade element (first electrode) 21 from outer blade element (second electrode) 23 of each blade 20, and may be made of any suitable material that has sufficient resistance to electrically insulate the two electrodes 21 and 23 as well as sufficient bonding strength for bonding together inner and outer blade elements 21 and 23. Outer blade element 23 of each blade 20 is preferably a thin metal plate or strip, such as stainless steel or aluminum. Inner blade element 21, insulative material 22, and outer blade element 23 have approximately the same width, each being within the range from 0.010 to 0.030 inch, and preferably about 0.020 inch each. The relatively small dimensions of blades 11 or other end effectors (e.g., forceps) employed with the instrument in accordance with the present invention facilitate the delicate task of harvesting IMAs or other arteries through minimally invasive incisions providing limited access.

FIGS. 4A–C show one possible blade configuration, in cross-section, as the blades close on tissue 40 to be severed. FIG. 4A depicts the blades as they first come into contact with tissue 40. The inside surface of inner blade element 21 defines the cutting edge 27 and shearing surface 28 of each blade 20. The outer surface and back edge of inner blade element 21 are covered by insulative material 22. Each blade 20 also includes an inside or forward tissue contacting edge surface 29 which includes inner blade element 21, insulating material 22, and outer blade element 23. In this embodiment, outer blade element 23 extends beyond inner blade element 21 and insulating material 22 to form an over-hanging lip 36 at the forward tissue contacting surface 29. Outer blade element 23 overlies only a portion of the outside surface of insulative material 22. Because the cutting edges 27 are of like polarity, there is no need to insulate the blades from one another.

As shown by the arrows 41 in FIG. 4A, when tissue contacting surface 29 of each blade comes into contact with tissue 40 to be cut, current flows primarily through tissue 40 between inner blade element 21 and outer blade element 23 of opposite blades. As the blades begin to cut tissue 40 and the distance between the blades decreases, as shown in FIG. 4B, current flows between inner blade element 21 and outer blade elements 23 of the same blade, as well as between outer blade element 23 and shearing surface 28 of inner blade element 21 of the other blade. The extent of current flow through the tissue in this situation may vary depending on the tissue type, position, thickness, and the extent to which the tissue is under tension. Finally, in FIG. 4C, when the blades are in a fully closed position, shearing surfaces 28 of the blades are in a face-to-face relationship with each other. In this position, the amount of current flow between outer blade elements 23 and inner blade elements 21 of opposite blades is minimized, with current flowing primarily between inner blade element 21 and outer blade element 23 of each blade along tissue contact surface 29.

Although a scissors mechanism having a pair of coacting blades has been shown in detail, other end effectors are contemplated for use with the present invention. In addition to alternate designs, the scissors mechanism just described or other end effectors employing a similar bipolar configuration may be used to promote coagulation during a blunt dissection or similar procedure, where the opening action of the end effectors is used to contact or spread tissue. Alternately, a single blade or end effector may be used to promote hemostasis of tissue. For embodiments employing a single end effector rather than a pair of coacting members, the relative movement of the end effector may be side-to-side or back-and-forth or may otherwise have active and inactive positions. For example, one embodiment may provide a scalpel which moves in an in-and-out motion from the distal end of the shaft.

Furthermore, although a preferred bipolar blade configuration has been discussed in detail, other bipolar configurations are applicable for use with the present invention, such as those bipolar designs disclosed in copending U.S. patent application having Ser. No. 08/593,148 which is hereby incorporated by reference. Monopolar configurations may also be employed with the present invention. With a monopolar configuration, only one electrode would be located on the end effector with a return electrode, in the form of a body plate, being located remotely from the end effector.

Referring now to FIGS. 5A and 5B, there are shown horizontal cross-sectional side views of the handle portion 2 and shaft portion 3, respectively, of instrument 1 described with respect to FIGS. 1A–B. Handle portion 2 and shaft 3 are tubular or have an inner lumen 50 which extends from scissors mechanism 4 into the proximal end of handle 2. Extending through and moveable within inner lumen 50 is an actuator rod 51 for opening and closing the blades of scissors mechanism 4. The distal end 15 of actuator rod 51 is slotted horizontally along the longitudinal axis of actuator rod 51 such that distal end 15 terminates into two posts 30. Posts 30 are attached to the ends of sliding pin 17 such that the proximal segments 25 (see FIG. 3) of inner blade elements 21 reside and are moveable within the longitudinal slot of actuator rod 51.

A cylindrical spring or coil 62 is positioned coaxially around the distal end 15 of rod 51 and resides within the spacing provided between a first busing 61 and a second bushing 63. Bushing 61 forms a portion of the body of shaft 3 and has internal diameter which is flush with lumen 50. Bushing 63 forms a portion of and is moveable along with rod 51. Cylindrical spring 62 serves to distally bias bushing 63 of rod 51 against an annular stopper 64 and to bias pin 17 to be positioned distally within slots 16 (see FIGS. 1C and 2) of blades 11 and maintain blades 11 in an open position.

The proximal end of rod 51 has an annular recess 55. Residing within annular recess 55 is a detent 56 which extends from the base portion 57 of lever 6. In an open blade position, lever 6 extends distally outward from cover 5 of handle 2 with base portion 57 biased against the distal wall 59 of a lever chamber 58. When lever 6 is pressed downward, lever 6 pivots about fulcrum 13 causing base portion 57 to abut proximal wall 60 of lever chamber 58 and pulling rod 51 backwards or proximally by means of detent 56. This causes pin 17 to move proximally within slots 16 which in turn causes blades 11 to close. Due to the spring bias against bushing 63, when lever 6 is released, rod 51 moves forward opening blades 11. Although particular linkage or components between the blades and handle have been described for effecting the opening and closing of the scissors mechanism, those skilled in the art will recognize that other comparable means and components for accomplishing relative movement between the end effectors.

Returning to FIG. 3, insulating material 22 and inner blade element 21 of each blade 20 preferably extend along the entire length of blade segments 24 and 25. Each outer blade element 23 extends only the length of blade segment 24 and is electrically coupled to a contact wire 32 (one per blade) by means of a weld point 31. Both contact wires 32, one for each blade 20, are encapsulated in inner 33 and outer 34 layers of insulating material, preferably Teflon shrink tubing, and are electrically insulated from shaft 30 and actuator rod 51, both of which are metal, preferably stainless steel. Within handle portion 2, as shown in FIG. 5A, insulated contact wires 32 extend along rod 51 within lumen 50 and are each electrically coupled to lead 10 at contact point 66. Thus, outer blade elements 23 (i.e., the second electrodes on each blade) are commonly polarized.

As shown in FIG. 5A, metal actuator rod 51 is shown to be in contact with conductive spring plate 65 which is electrically coupled to lead 9 at contact point 67. As such, inner blade elements 21 (i.e., the first electrodes on each blade) are commonly polarized but have a polarity which is opposite to that of outer blade elements 23 (i.e., the second electrodes on each blade). Alternately, actuator rod 51 may be in a spaced-apart relationship with spring plate 65. In this configuration, actuating or depressing lever 6 causes rod 51 to contact spring plate 65 closing the electrical circuit with the RF energy source and causing inner blade elements 21 (i.e., the first electrodes on each blade) to become. With either configuration, both pairs of electrodes 21 and 23 are oppositely polarized and current may flow between the first and second electrodes on the same blade as well as between the first electrode of one blade and the second electrode of the other blade.

Referring now to FIG. 6, there is shown a perspective view of a preferred embodiment of a handle portion 70 of an electrosurgical instrument in accordance with the present invention. Handle portion 70 has a cover 71 and an actuator lever 72 mounted therein as described above. On the top surface 74 of lever 72 are located two adjacent actuators 75 and 76, each providing a different mode of operation.

Actuator 75 is in the form of a depressible button or trigger but may also be a slide switch or other like mechanism. Actuator button 75 has a first depressible position which causes the first electrodes (inner blade elements) of each blade to be electrically coupled to one of the two bipolar terminals of an RF voltage source (not shown) and the second electrodes (outer blade elements) of each blade to be electrically coupled to the other bipolar while the blades of the scissor mechanism remain in an inactive or open position. For a scissors mechanism having only one electrode coupled to each blade, where the electrodes are of opposite polarity, the first depressible position causes one blade to be electrically coupled to one terminal of the voltage source and the other blade to be electrically coupled to the other terminal of the voltage source. In either case, the electrical coupling may be accomplished with an electrical contact mechanism, such as the conductive contact spring discussed above, and a contact wire which runs from first actuator 75 to the voltage source. No change in the physical position of actuator lever 72 is necessary to effect this coupling.

In this preferred embodiment, actuator button 75 also has a second depressible position wherein the bias imposed on lever 72 (as a result of a cylindrical spring acting on the actuator rod, discussed above with respect to FIG. 5B) is overcome, causing lever 72 to pivot about fulcrum 77 which in turn causes the actuator rod to retract, pulling close the blades of the electrosurgical instrument. In the embodiment just described, the force necessary to achieve the first depressible position is less than the force necessary to achieve the second depressible position, providing application of bipolar energy followed by actuation of the scissor blades from an open to a closed position. This sequential application of bipolar energy and scissor action is allows the end effector to be used solely as a cautery device. Conversely, the present invention may be adapted to provide the simultaneous application of electrosurgical energy and mechanical action of the end effector.

Alternatively, a second mode of operation may also be provided by means of a second actuator 76, which is shown in the form of a beveled trigger or button. Actuation of trigger 76 causes lever 72 to pivot about fulcrum 77, causing the actuator rod to retract, and thus close the scissor blades without transmitting bipolar energy between the electrodes. First actuator button 75 is raised from the surface of lever 72 and second actuator button 76 is beveled or recedes from or flush with the surface of lever 72, or visa versa, so that a user may be able to distinguish the two by touch alone.

As shown in FIG. 6, preferably lever 72 has a low profile and both actuator buttons or triggers 75 and 76 are operable by the tip of only one finger, such as the index finger of the hand in which the instrument is held, but may also be operable by more than one finger if desired. This stream lined, ergonomic positioning and design of lever 72 and actuators 75, 76 is advantageously less cumbersome and fatiguing than pistol grip actuators, and allows improved freedom of movement in minimally invasive harvesting of bypass grafts. Additionally, the fingertip actuation configuration of the present invention, tends to be more sensitive and therefore is capable of providing more precise control of the actuators, especially in the deliverance of bipolar energy. This is crucial in harvesting IMAs and other arteries through a minimally invasive incision in which vision and access are limited, and the risk of damage to the artery is high.

The fingertip actuation design of the present invention is also particularly advantageous in combination with the ability of the instrument's shaft to be rotated by rotation mechanism 78. This combination allows multiple orientations of the blades or end effectors with respect to the harvesting site as well as within the user's hand, obviating the need for the user to rotate the instrument within his hand, switch the instrument to his other hand (which may not be as dexterous), change his or her position with respect to the target site, use multiple instruments having different configurations, or use more than one finger to actuate blade movement and bipolar energy.

Although button actuators have been described, other types of actuators, such as loops, pull triggers, pedals, or other depressible mechanisms, such as those which are operable by the thumb or foot, may also be employed with the electrosurgical instrument of the present invention. For example, an alternate embodiment includes a first actuator, similar to actuator 75 described above with respect to FIG. 6, and a second actuator in the form of a trigger located on the instrument handle and operable by either a finger or thumb for mechanical actuation of the scissors mechanism. Alternately, the second actuator may comprise a foot pedal which is electrically connected to the blades by means of a cable for actuating the relative movement of the blades.

The particular examples set forth herein are instructional and should not be interpreted as limitations on the structure of the invention or on the applications to which those of ordinary skill are able to apply this invention. It will be readily apparent to those skilled in the art that certain modifications and other embodiments may be practiced without departing from the spirit and scope of the invention and which are within the scope of the appended claims.

What is claimed is:

1. A bipolar electrosurgical tool comprising:
   an elongated shaft having proximal and distal ends:
   a pair of blades joined for relative movement and sequential actuation of current flow wherein said relative movement is in a scissor-like action between open and closed positions at said distal end of said shaft, each said blade comprising first and second spaced apart electrodes extending along said blade, said electrodes being adapted for connection to a voltage source having a pair of terminals of opposite polarity whereby current flow between said first and second electrodes of each blade promotes hemostasis in tissue contacting said blades;
   a handle operatively connected to said proximal end of said shaft; and at least one actuator operably connected to said blades and positioned on said handle to be operable by a user's fingertip on the hand with which said tool is held for effecting said relative movement of said blades and for actuating current flow through said electrodes of each blade wherein said at least one actuator is comprised of a first depressible position for causing said first electrodes to be connected to one terminal and said second electrodes to be connected to the other terminal of said voltage source, and a second depressible position for causing said blades to close.

2. The bipolar electrosurgical tool of claim 1 wherein the force necessary to achieve said first depressible position is less than the force necessary to achieve said second depressible position.

3. The bipolar electrosurgical tool of claim 2 wherein said at least one actuator comprises a lever having a proximal end and a distal end, said proximal end being pivotally coupled to said handle and said distal end extending distally and outwardly from said handle at an acute angle therewith.

4. The bipolar electrosurgical tool of claim 1 further comprising a second actuator connected to cause said blades to close.

5. The bipolar electrosurgical tool of claim 4 wherein each of said actuators are operable by the same finger.

6. The bipolar electrosurgical tool of claim 5 wherein each of said actuators are adjacent buttons on a lever having a proximal end and a distal end, said proximal end being pivotally coupled to said handle and said distal end extending distally and outwardly from said handle at an acute angle therewith.

7. The bipolar electrosurgical tool of claim 4 wherein one of said actuators is operable by the user's thumb and the other said actuator is operable by a user's finger other than the thumb.

8. A bipolar electrosurgical tool comprising:
   an elongated shaft having proximal and distal ends;
   a pair of blades joined for relative movement in a scissor-like action between open and closed positions at said distal end of said shaft, each said blade comprising first and second spaced apart electrodes extending along said blade, said electrodes being adapted for connection to a voltage source having a pair of terminals of opposite polarity whereby current flow between said first and second electrodes of each blade promotes hemostasis in tissue contacting said blades;
   a handle operatively connected to said proximal end of said shaft; and
   at least two actuators operably connected to said blades wherein a first actuator is positioned on said handle to be operable by one of a user's fingertip on the hand with which said tool is held for actuating said relative movement of said blades, and wherein a second actuator is operably connected to said blades and positioned to be operable by a user's foot for actuating said relative movement of said blades and for actuating current flow through said electrodes of each blade.

9. A method for harvesting a vessel comprising the steps of:
   providing an instrument comprising a pair of distal coacting members joined for relative movement between open and closed positions and further comprising at least one depressible actuator operably connected to said distal coacting members and having first and second depressible positions wherein depressing said actuator to achieve said first depressible position provides current flow between said members and depressing said actuator to achieve said second depressible position actuates said relative movement;
   contacting tissue adjacent the vessel with said distal coacting members;
   depressing said actuator with a finger;
   providing current flow between said members;
   actuating said relative movement.

* * * * *